United States Patent [19]

Aoyagi et al.

[11] Patent Number: 5,720,284
[45] Date of Patent: Feb. 24, 1998

[54] APPARATUS FOR MEASURING HEMOGLOBIN

[75] Inventors: Takuo Aoyagi; Masayoshi Fuse; Michio Kanemoto; Cheng Tai Xie, all of Tokyo, Japan

[73] Assignee: Nihon Kohden Corporation, Tokyo, Japan

[21] Appl. No.: 623,862

[22] Filed: Mar. 29, 1996

[30] Foreign Application Priority Data

Mar. 31, 1995 [JP] Japan .................. 7-076888

[51] Int. Cl.⁶ .................................................. A61B 5/00
[52] U.S. Cl. .................................................. 128/633
[58] Field of Search .................. 128/633, 664; 356/39–41

[56] References Cited

U.S. PATENT DOCUMENTS

| | | | |
|---|---|---|---|
| 5,101,825 | 4/1992 | Gravenstein et al. | 128/633 |
| 5,277,181 | 1/1994 | Mendelson et al. | 128/633 |
| 5,372,136 | 12/1994 | Steuer et al. | 128/633 |

FOREIGN PATENT DOCUMENTS 3-71135  11/1991  Japan .

OTHER PUBLICATIONS

"Theoretical and Experimental Study on Optical Density of Blood", Japanese Journal of Medical Electronics and Biological Engineering, vol. 30, No. 1 pp. 1–7.

*Primary Examiner*—Jennifer Bahr
*Assistant Examiner*—Eric F. Winakur
*Attorney, Agent, or Firm*—Sughrue, Mion, Zinn, Macpeak & Seas, PLLC

[57] ABSTRACT

Light of various wavelengths emitted from light sources and transmitted through vital tissues is converted by light sensors and current/voltage transducers, into electric signals. The signals are converted into digital values by an A/D converter. The light source emits light of a wavelength which can be optically absorbed by water. A computer obtains a ratio of variations of the digital values for each wavelength, and calculates the values of tissue terms and the hemoglobin concentration on the basis of the ratios. In the calculation, since tissue terms of the wavelengths have mutual constant relationships, an equation which is prepared so that there exists only one unknown in the tissue terms is used.

1 Claim, 7 Drawing Sheets

APPARATUS FOR MEASURING HEMOGLOBIN

BACKGROUND OF THE INVENTION

The invention relates to an apparatus for measuring noninvasively and continuously the hemoglobin concentration in the blood.

Importance of the measurement of the hemoglobin concentration will be described.

1. In the Case of Chronic Variation

Hemoglobin in the blood is reversely bound to oxygen and flows through in a blood vessel so that oxygen is supplied to the whole body. When the hemoglobin concentration in the blood is abnormally low, or when a person is anemic, therefore, the supply of oxygen to the tissues becomes insufficient. Hemoglobin in the blood exists in red blood cells. When the hemoglobin concentration in the blood is abnormally high, therefore, the viscosity of the blood is increased so that the blood hardly flows. Since also an apparently healthy person may have such an abnormality of the hemoglobin concentration, it is necessary to periodically subject a healthy person to the measurement of the hemoglobin concentration. Also a patient scheduled for operation is required to be measured in hemoglobin concentration. In order to satisfy such requirements, it is an important factor that the measurement of the hemoglobin concentration is conducted noninvasively and accepted by a wide range of subjects without resistance.

2. In the Case of Acute Variation

During an operation, there occurs bleeding so that the circulatory blood volume is reduced. As a treatment against this phenomenon, blood transfusion or infusion is conducted. The criterion for judging the use of either of the two countermeasures is based on the measurement of the hemoglobin concentration. Consequently, the continuous measurement of the hemoglobin concentration during an operation is very important. When a patient of renal failure is subjected to dialysis, the variation in hemoglobin concentration is an important matter of concern. Also in such a case, the continuous measurement of the hemoglobin concentration is very important.

3. In the Case Where the Concentration of an Optical Absorptive Substance in the Blood is Measured In some cases such as where the cardiac output is to be calculated, the concentration of a pigment injected into the blood or that of an optical absorptive substance in the blood is obtained. In such a case, it is convenient to obtain a ratio of optical absorption of the optical absorptive substance in the blood to that of hemoglobin and multiply the ratio by the hemoglobin concentration. Consequently, the measurement of the hemoglobin concentration is important.

Next, kinds of hemoglobin will be described. There are many kinds of hemoglobin. Each kind of hemoglobin has intrinsic optical absorptive characteristics (wavelength characteristics of optical absorption). The term of a hemoglobin meter means an apparatus for measuring the total hemoglobin concentration. The cyanmethemoglobin method is employed as a standard method of measuring hemoglobin. In this method, all kinds of hemoglobin are converted by a chemical reaction into cyanmethemoglobin and the resulting cyanmethemoglobin is optically measured.

In an apparatus which is so-called "CO-oxymeter," various kinds of hemoglobin are measured as they are, and the total sum of the measure values is then obtained as the total hemoglobin concentration. Specifically, a specimen is placed in a cell having a predetermined thickness, optical absorptive characteristics for a plurality of light wavelengths are measured, concentrations of each kinds of hemoglobin are calculated, and then the total sum of the concentrations is obtained. In this case, the four kinds of hemoglobin described below are usually employed as measuring objects.

Namely, the measuring objects are oxyhemoglobin, reduced hemoglobin, carboxyhemoglobin, and methemoglobin.

In a prior art apparatus for measuring hemoglobin using such a method, the blood must be collected and hence the measurement cannot be continuously conducted. In contrast, an apparatus using the pulse method can measure the hemoglobin concentration noninvasively and continuously. An example of the measuring apparatus is disclosed in Japanese Patent Publication (Kokoku) No. Hei.3-71135.

However, in the measuring apparatus, it is assumed that layers of vital tissues other than the blood layer (hereinafter, such layers are referred to as "tissue layers") are not caused to pulsate by pulsation of the blood and always have a constant thickness. In reality, however, their thickness is varied in accordance with pulsation of the blood. Consequently, a measure value has an error due to the variation.

SUMMARY OF THE INVENTION

It is an object of the invention to provide an apparatus which can non-invasively, continuously and accurately measure the hemoglobin concentration in due consideration of the variation in thickness of tissue layers.

According to the invention, the apparatus comprises: light irradiating means for irradiating vital tissues with light having different wavelengths, at least one of the wavelengths being able to be optically absorbed by water; photoelectric converting means for converting light which is emitted from the light irradiating means and transmitted through the vital tissues, into an electric signal; optical density variation calculating means for obtaining an optical density variation for each of the wavelengths from pulsation of an output of the photoelectric converting means, the optical density variation being a difference between pulsation due to blood and pulsation due to the tissues; optical density ratio calculating means for obtaining a ratio of optical density variations for the wavelengths which are obtained by the optical density variation calculating means; and hemoglobin concentration calculating means for obtaining a total hemoglobin concentration and/or respective hemoglobin concentrations from an output of the optical density ratio calculating means.

In the invention, light emitted from the light irradiating means and impinged on vital tissues is transmitted through the vital tissues and then converted into an electric signal by the photoelectric converting means. From pulsation of the output of the photoelectric converting means, the optical density variation calculating means obtains a optical density variation for each of the wavelengths which is a difference between pulsation due to blood and pulsation due to the tissue. The optical density ratio calculating means obtains a ratio of optical density variations for the wavelengths which are obtained by the optical density variation calculating means. The hemoglobin concentration calculating means obtains the total hemoglobin concentration and/or respective hemoglobin concentrations from the output of the optical density ratio calculating means.

In the invention, a wavelength which can be optically absorbed by water is used. Therefore, water contained in the blood is handled as one of optical absorptive substances, thereby obtaining the hemoglobin concentration with respect to water. The hemoglobin concentration with respect to water is an absolute concentration.

DETAILED DESCRIPTION OF THE PREFERRED EMBODIMENTS

First, the principle common to all embodiments will be described. In the embodiments, the pulse method is used. In the pulse method, the phenomenon in which the effective thickness of the blood is caused to pulsate by blood pulsation in the vital tissues is used, and the optical absorptive characteristics of the blood in the tissues are measured while irradiating the vital tissues with light. Since the kinds of hemoglobin have different optical absorptive characteristics, the total hemoglobin concentrations in the blood and then calculating the total sum of the concentrations. Therefore, the number of light wavelengths required for the measurement depends on that of kinds of hemoglobin contained in the blood.

The measurement of an absolute value of the hemoglobin concentration requires the thickness of the specimen. In the pulse method, the thickness of the blood to be measured is not known, and hence the thickness is measured by measuring optical absorption of water in the blood while deeming the thickness of the blood as that of water. Consequently, it is necessary to use a wavelength which can be optically absorbed by water. It is sufficient for the measurement to use only one wavelength at which optical absorption of water is sufficiently large.

In accordance with pulsation of the blood in the tissues, vital tissues other than the blood (hereinafter, such tissues are referred to as pure "tissues") pulsate. The pulsation of the optical density due to the pulsation of the pure tissues is superposed on that of the optical density due to the blood. As a result, when the calculation is performed under assumption that only the thickness of the blood contributes to the pulsation, a large error is produced. In the measurement of the total hemoglobin concentration, therefore, it is an important problem to eliminate influence of the pulsation of the pure tissues. The values of pulsation terms of pure tissues in a theoretical expression are varied depending on the wavelength, but have mutual constant relationships so that it is possible to assume there exists only one unknown. Therefore, one wavelength is required for obtaining the tissue term.

The four above-mentioned kinds of hemoglobin are indicated by the symbols as follows:

| Substance: | Symbol of concentration in blood: | Absorption coefficient |
|---|---|---|
| Oxyhemoglobin (O₂Hb) | SoHb | Eo |
| Reduced hemoglobin (RHb) | SrHb | Er |
| Carboxyhemoglobin (COHb) | ScHb | Ec |
| Methemoglobin (MetHb) | SmHb | Em |
| Total hemoglobin (Hb) | Hb | |
| Water | Cw | Ew |

In the above,
Hb=O₂Hb+RHb+COHb+MetHb=(So+Sr+Sc+Sm)Hb,
and
So+Sr+Sc+Sm=1

Figure 6:
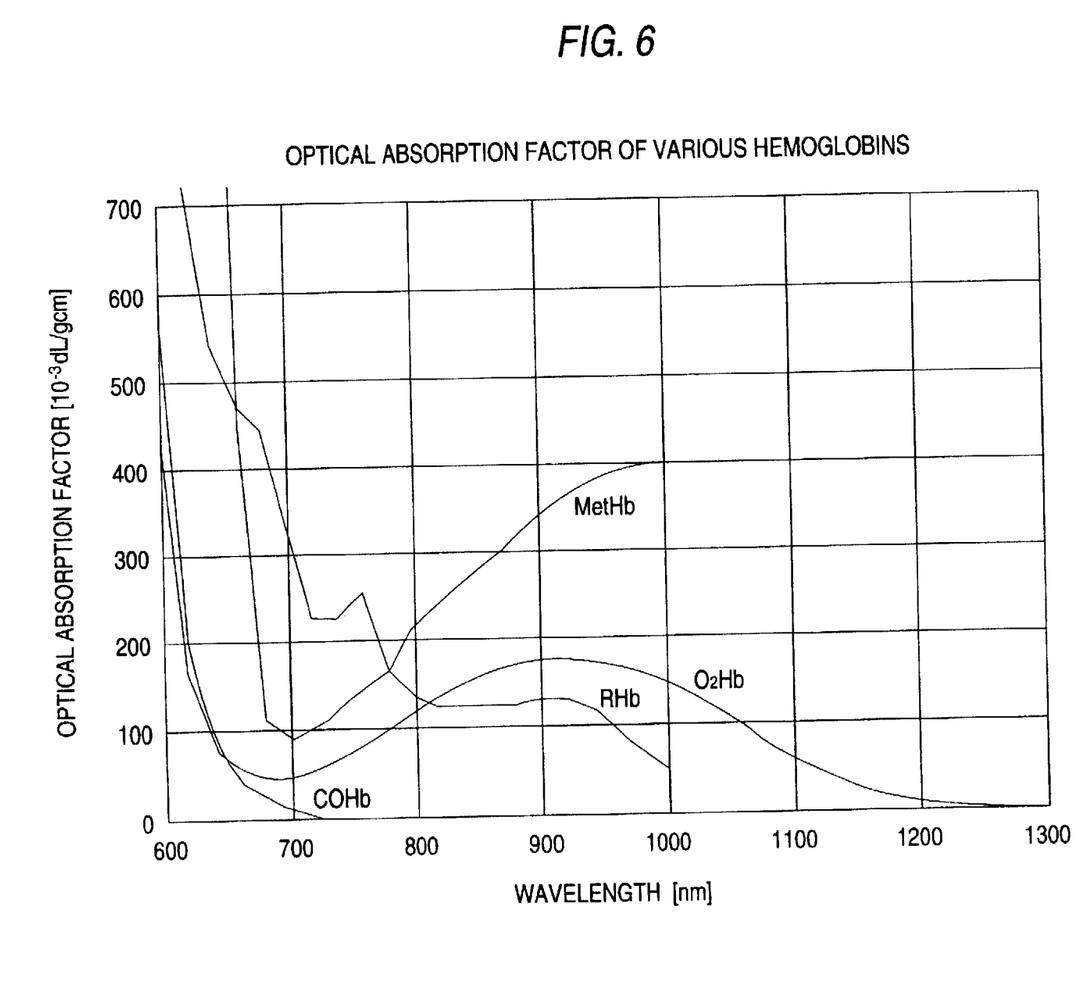
FIG. 6 is a graph showing relationships between optical absorption factors of various hemoglobins and wavelength.
Figure 7:
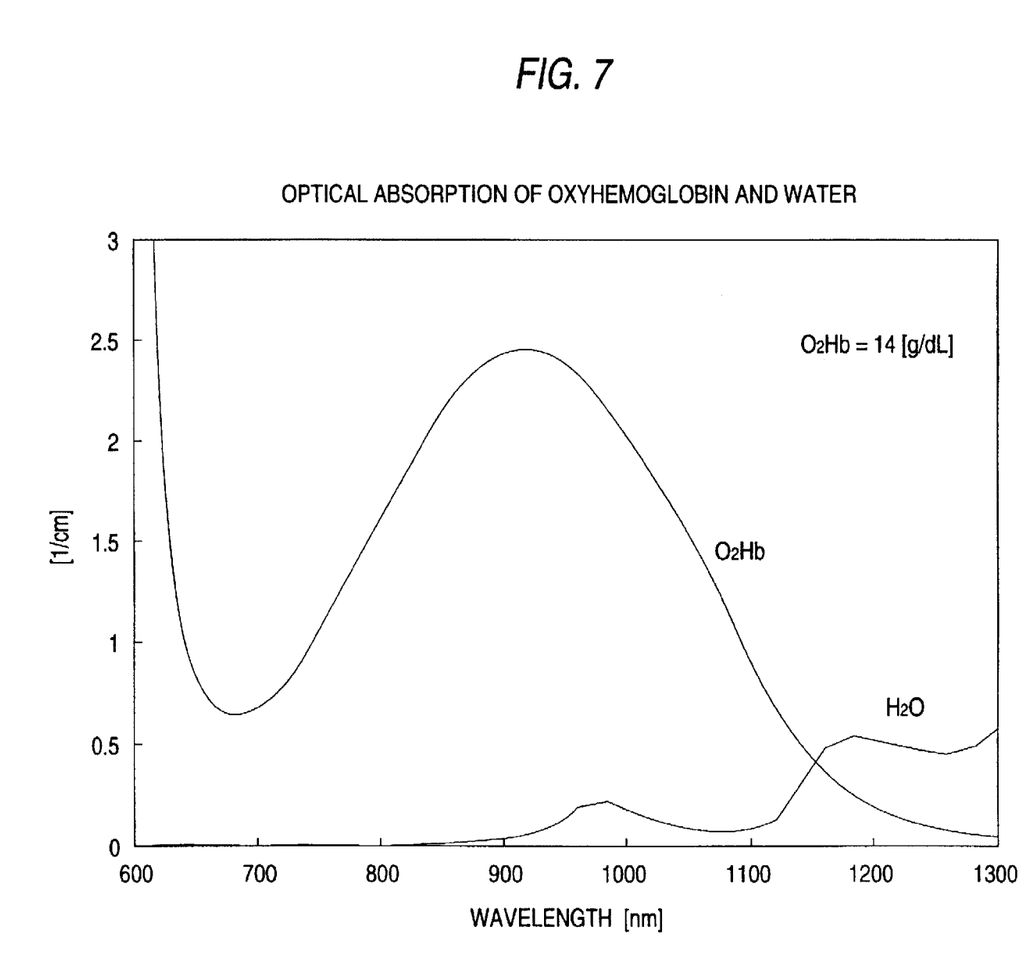
FIG. 7 is a graph showing relationships between wavelength and optical absorption of hemoglobin and water.

FIG. 6 shows optical absorptive characteristics of various kinds of hemoglobin, and FIG. 7 shows optical absorption of water with respect to that of oxyhemoglobin in the case where the hemoglobin concentration is 14 [g/dL].

The principle of a first embodiment will be described. The embodiment is directed to an apparatus which is to be used in the case where only oxyhemoglobin and reduced hemoglobin exist as hemoglobin in the blood. In this case, four light wavelengths are used and the following simultaneous equations with three unknowns are employed:

$$\Phi_{12} = [\{(Eo_1So + Er_1Sr + Ew_1CW/Hb)(Eo_1So + Er_1Sr + \quad (1)$$

$$Ew_1CW/Hb + F)\}^{1/2} - Ex_1]/[\{(Eo_2So + Er_2Sr + Ew_2CW/Hb)(Eo_2So + $$

$$Er_2Sr + Ew_2CW/Hb + F)\}^{1/2} - Ex_2]$$

$$\Phi_{32} = [\{(Eo_3So + Er_3Sr + Ew_3CW/Hb)(Eo_3So + Er_3Sr + \quad (2)$$

$$Ew_3CW/Hb + F)\}^{1/2} - Ex_3]/[\{(Eo_2So + Er_2Sr + Ew_2CW/Hb)(Eo_2So + $$

$$Er_2Sr + Ew_2CW/Hb + F)\}^{1/2} - Ex_2]$$

$$\Phi_{42} = [\{(Eo_4So + Er_4Sr + Ew_4CW/Hb)(Eo_4So + Er_4Sr + \quad (3)$$

$$Ew_4CW/Hb + F)\}^{1/2} - Ex_4]/[\{(Eo_2So + Er_2Sr + Ew_2CW/Hb)(Eo_2So + $$

$$Er_2Sr + Ew_2CW/Hb + F)\}^{1/2} - Ex_2]$$

Next, the ground of the equations will be described.

The optical density of the blood in the tissues is similar to that produced when scattering enters a thin blood layer. It was confirmed theoretically and experimentally that, when the optical density was measured by using a spectrophotometer into which an integral sphere is integrated, the following equation is held:

$$\Delta Ab = \{(EhHb+EwCw)(EhHb+EwCw+FHb)\}^{1/2} \cdot \Delta Db$$

where

Eh: optical absorption coefficient of hemoglobin,

ΔDb: variation of the effective thickness of the blood, and

ΔAb: variation of the optical density due to ΔDb.

The relationship of expression (4) is described in "THEORETICAL AND EXPERIMENTAL STUDY ON OPTICAL DENSITY OF BLOOD," by Takuo Aoyagi, Japanese Journal of Medical Electronics and Biological Engineering, 30(1), 1–7 (1992).

The intensity of transmitted light pulsates in accordance with pulsation of the blood in the tissues. This seems to be caused not only by pulsation of the effective thickness of the blood in the tissues but also by other phenomena which mainly include pulsation of the effective thickness of tissues other than the blood or the pure tissues. The latter pulsation is produced in a phase opposite to that of pulsation of the blood. Accordingly, the variation ΔA of the optical density of the vital tissues can be expressed as follows:

$$\Delta A = \Delta Ab - \Delta At \qquad (5)$$
$$= \{(EhHb + EwCw)(EhHb + EwCw + Fhb)\}^{1/2} \cdot \Delta Db - Zt\Delta Dt$$

where $\Delta at$: variation of the optical density of the pure tissues, $\Delta Dt$: variation of the effective thickness of the pure tissues, and $Zt$: optical reduction rate of the pure tissues.

By using the intensity of transmitted light I, $\Delta A$ can be expressed:

$$\Delta A = \log\{I/(I-\Delta I)\} \qquad (5A)$$

This expression can be approximated as follows:

$$66\ A = \Delta I/I \qquad (5B)$$

When $\Delta A$ is measured by using light of two wavelengths of $\lambda_1$ and $\lambda_2$, the ratio $\Phi_{12}$ is obtained as follows:

$$\begin{aligned}\Phi_{12} &= \Delta A_1/\Delta A_2 \qquad (6A)\\ &= [\{(Eo_1So + Er_1Sr + Ew_1CW/Hb)(Eo_1So + Er_1Sr + \\ &\quad Ew_1CW/Hb + F)\}^{1/2} - Ex_1]/[\{(Eo_2So + \\ &\quad Er_2Sr + Ew_2CW/Hb)(Eo_2So + Er_2Sr + \\ &\quad Ew_2CW/Hb + F)\}^{1/2} - Ex_2]\end{aligned}$$

where $Ex_1$ and $Ex_2$ are:

$$Ex_1=(Zt_{1/Hb})(\Delta Dt/\Delta Db)\ \text{and}\ Ex_2=(Zt_{2/Hb})(\Delta Dt/\Delta Db) \qquad (6B)$$

In reality, the values of $Ex_1$ and $Ex_2$ contain an error factor, but there is a relationship between $Ex_1$ and $Ex_2$ which can be deemed as constant including the error factors in a practical view point. When the relationship is once measured, therefore, it can be used in the calculation.

In the specification, a term of an equation such as $\{(Eo_1So+Er_1Sr+Ew_1CW/Hb)(Eo_1So+Er_1Sr+Ew_1CW/Hb+F)\}^{1/2}$ of equation (6) which relates to the blood is referred to as a blood term, and a term such as $Ex_1$ which relates to the pure tissues is referred to as a tissue term.

In the above, $\Phi_{12}$ of equation (1) has been described. This description is also applicable to $\Phi_{32}$ and $\Phi_{42}$ of equations (2) and (3).

The tissue terms $Ex_1$, $Ex_2$, $Ex_3$, and $Ex_4$ have different values depending on measurement conditions. When $Ex_2$ is once determined, for example, the other tissue terms can be obtained from $Ex_2$ on the basis of constant mutual relationships among $Ex_1$, $Ex_2$, $Ex_3$, and $Ex_4$. Generally, the terms can be written as follows:

$$Ex_1 = f_1(Ex_2) \qquad (7)$$
$$Ex_3 = f_3(Ex_2) \qquad (8)$$
$$Ex_4 = f_4(Ex_2) \qquad (9)$$

Practically, relationships of equations of 1st degree can be used in the following manner:

$$Ex_1 = A_1Ex_2 + B_1 \qquad (10)$$
$$Ex_3 = A_3Ex_2 + B_3 \qquad (11)$$
$$Ex_4 = A_4Ex_2 + B_4 \qquad (12)$$

In the equations, $A_1$, $A_3$, $A_4$, $B_1$, $B_3$, and $B_4$ are known. As described above, it is assumed that only oxyhemoglobin and reduced hemoglobin exist as hemoglobin. Therefore, the following equation is held:

$$Sr = 1 - So \qquad (13)$$

By substituting equations (10) to (13) into equations (1) to (3), simultaneous equations with three unknowns So, $Ex_2$, and Hb are obtained. When the simultaneous equations are solved, the values of So, $Ex_2$, and Hb can be obtained. This is set as a first embodiment (A).

In the embodiment, So and Sr can be made 1 and 0, respectively, by suitably selecting a light wavelength at which an effect of the oxygen saturation can be neglected. Consequently, there remain two unknowns $EX_2$ and Hb to be obtained. As a result, Hb can be obtained from simultaneous equations with two unknowns which use three wavelengths.

In this case, the following equations are held:

$$\Phi_{12}=[\{(Eo_1+Ew_1CW/Hb)(Eo_1+Ew_1CW/Hb+F)\}^{1/2}-Ex_1]/[\{(Eo_2+Ew_2CW/Hb)(Eo_2+Ew_2CW/Hb+F)\}^{1/2}-Ex_2] \qquad (1A)$$

$$\Phi_{32}=[\{(Eo_3+Ew_3CW/Hb)(Eo_3+Ew_3CW/Hb+F)\}^{1/2}-Ex_3]/[\{(Eo_2+Ew_2CW/Hb)(Eo_2+Ew_2CW/Hb+F)\}^{1/2}-Ex_2] \qquad (2A)$$

This is set as a first embodiment (B).

Next, the principle of a second embodiment will be described. The embodiment is directed to an apparatus which is to be used in the case where oxyhemoglobin, reduced hemoglobin, and carboxyhemoglobin exist as hemoglobin in the blood. In this case, five light wavelengths are used and the following simultaneous equations with four unknowns are employed.

$$\begin{aligned}\Phi_{12} = &[\{(Eo_1So + Er_1Sr + Ec_1Sc + Ew_1CW/Hb)(Eo_1So + Er_1Sr + \\ &Ec_1Sc + Ew_1CW/Hb + F)\}^{1/2} - Ex_1]/[\{(Eo_2So + Er_2Sr + Ec_2Sc + \\ &Ew_2CW/Hb)(Eo_2So + Er_2Sr + Ec_2Sc + Ew_2CW/Hb + F)\}^{1/2} - Ex_2]\end{aligned} \qquad (14)$$

$$\begin{aligned}\Phi_{32} = &[\{(Eo_3So + Er_3Sr + Ec_3Sc + Ew_3CW/Hb)(Eo_3So + Er_3Sr + \\ &Ec_3Sc + Ew_3CW/Hb + F)\}^{1/2} - Ex_3]/[\{(Eo_2So + Er_2Sr + Ec_2Sc + \\ &Ew_2CW/Hb)(Eo_2So + Er_2Sr + Ec_2Sc + Ew_2CW/Hb + F)\}^{1/2} - Ex_2]\end{aligned} \qquad (15)$$

$$\begin{aligned}\Phi_{42} = &[\{(Eo_4So + Er_4Sr + Ec_4Sc + Ew_4CW/Hb)(Eo_4So + Er_4Sr + \\ &Ec_4Sc + Ew_4CW/Hb + F)\}^{1/2} - Ex_4]/[\{(Eo_2So + Er_2Sr + Ec_2Sc + \\ &Ew_2CW/Hb)(Eo_2So + Er_2Sr + Ec_2Sc + Ew_2CW/Hb + F)\}^{1/2} - Ex_2]\end{aligned} \qquad (16)$$

$$\begin{aligned}\Phi_{52} = &[\{(Eo_5So + Er_5Sr + Ec_5Sc + Ew_5CW/Hb)(Eo_5So + Er_5Sr + \\ &Ec_5Sc + Ew_5CW/Hb + F)\}^{1/2} - Ex_5]/[\{(Eo_2So + Er_2Sr + Ec_2Sc + \\ &Ew_2CW/Hb)(Eo_2So + Er_2Sr + Ec_2Sc + Ew_2CW/Hb + F)\}^{1/2} - Ex_2]\end{aligned} \qquad (17)$$

In the embodiment, in addition to equations (10) to (12), the following relationship is established among the tissue terms $Ex_i$ ($i = 1, 2, 3, 4,$ and 5):

$$Ex_5 = A_5Ex_2 + B_5 \qquad (18)$$

where $A_5$ and $B_5$ are known.

In this case, the following equation is held:

$$Sr = 1 - So - Sc \qquad (19)$$

By substituting equations (10) to (12), (18), and (19) into equations (14) to (17), simultaneous equations with four unknowns So, Sc, $EX_2$, and Hb are obtained. When the simultaneous equations are solved, the values of So, Sc, $Ex_2$, and Hb can be obtained.

Next, a third embodiment will be described. When there exists methemoglobin in place of carboxyhemoglobin in the second embodiment, equations corresponding to equations (14) to (17) are as follows:

$$\Phi_{12} = [\{(Eo_1So + Er_1Sr + Em_1Sm + Ew_1CW/Hb)(Eo_1So + Er_1Sr + \quad (14A)$$
$$Em_1Sm + Ew_1CW/Hb + F)\}^{1/2} - Ex_1]/[\{(Eo_2So + Er_2Sr + Em_2Sm +$$
$$Ew_2CW/Hb)(Eo_2So + Er_2Sr + Em_2Sm + Ew_2CW/Hb + F)\}^{1/2} - Ex_2]$$

$$\Phi_{32} = [\{(Eo_3So + Er_3Sr + Em_3Sm + Ew_3CW/Hb)(Eo_3So + Er_3Sr + \quad (15A)$$
$$Em_3Sm + Ew_3CW/Hb + F)\}^{1/2} - Ex_3]/[\{(Eo_2So + Er_2Sr + Em_2Sm +$$
$$Ew_2CW/Hb)(Eo_2So + Er_2Sr + Em_2Sm + Ew_2CW/Hb + F)\}^{1/2} - Ex_2]$$

$$\Phi_{42} = [\{(Eo_4So + Er_4Sr + Em_4Sm + Ew_4CW/hb)(Eo_4So + Er_4Sr + \quad (16A)$$
$$Em_4Sm + Ew_4CW/Hb + F)\}^{1/2} - Ex_4]/[\{(Eo_2So + Er_2Sr + Em_2Sm +$$
$$Ew_2CW/Hb)(Eo_2So + Er_2Sr + Em_2Sm + Ew_2CW/Hb + F)\}^{1/2} - Ex_2]$$

$$\Phi_{52} = [\{(Eo_5So + Er_5Sr + Em_5Sm + Ew_5CW/Hb)(Eo_5So + Er_5Sr + \quad (17A)$$
$$Em_5Sm + Ew_5CW/Hb + F)\}^{1/2} - Ex_5]/[\{(Eo_2So + Er_2Sr + Em_2Sm +$$
$$Ew_2CW/Hb)(Eo_2So + Er_2Sr + Em_2Sm + Ew_2CW/Hb + F)\}^{1/2} - Ex_2]$$

In the embodiment, the same relationship as that in the case of carboxyhemoglobin is established among the tissue terms $Ex_i$ (i=1, 2, 3, 4, and 5).

In this case, the following equation is held:

$$Sr = 1 - So - Sm \quad (19A)$$

By substituting equations (10) to (12), (18), and (19A) into equations (14A) to (17A), simultaneous equations with four unknowns So, Sm, $Ex_2$, and Hb are obtained. When the simultaneous equations are solved, the values of So, Sm, $Ex_2$, and Hb can be obtained.

Next, the principle of a fourth embodiment will be described. The embodiment is directed to an apparatus which is to be used in the case where oxyhemoglobin, reduced hemoglobin, carboxyhemoglobin, and methemoglobin exist as hemoglobin in the blood. In this case, six light wavelengths are used and the following simultaneous equations with five unknowns are employed:

$$\Phi_{12} = [\{(Eo_1So + Er_1Sr + Ec_1Sc + Em_1Sm + Ew_1CW/Hb)(Eo_1So + \quad (20)$$
$$Er_1Sr + Ec_1Sc + Em_1Sm + Ew_1CW/Hb + F)\}^{1/2} - Ex_1]/[\{(Eo_2So +$$
$$Er_2Sr + Ec_2Sc + Em_2Sm + Ew_2CW/Hb)(Eo_2So + Er_2Sr + Ec_2Sc +$$
$$Em_2Sm + Ew_2CW/Hb + F)\}^{1/2} - Ex_2]$$

$$\Phi_{32} = [\{(Eo_3So = Er_3Sr + Ec_3Sc + Em_3Sm + Ew_3CW/Hb)(Eo_3So + \quad (21)$$
$$Er_3Sr + Ec_3Sc + Em_3Sm + Ew_3CW/Hb + F)\}^{1/2} - Ex_3]/[\{(Eo_2So +$$
$$Er_2Sr + Ec_2Sc + Em_2Sm + Ew_2CW/Hb)(Eo_2So + Er_2Sr + Ec_2Sc +$$
$$Em_2Sm + Ew_2CW/Hb + F)\}^{1/2} - Ex_2]$$

$$\Phi_{42} = [\{(Eo_4So + Er_4Sr + Ec_4Sc + Em_4Sm + Ew_4CW/Hb)(Eo_4So + \quad (22)$$
$$Er_4Sr + Ec_4Sc + Em_4Sm + Ew_4CW/Hb + F)\}^{1/2} - Ex_4]/[\{(Eo_2So +$$
$$Er_2Sr + Ec_2Sc + Em_2Sm + Ew_2CW/Hb)(Eo_2So + Er_2Sr + Ec_2Sc +$$
$$Em_2Sm + Ew_2CW/Hb + F)\}^{1/2} - Ex_2]$$

$$\Phi_{52} = [\{(Eo_5So + Er_5Sr + Ec_5Sc + Em_5Sm + Ew_5CW/Hb)(Eo_5So + \quad (23)$$
$$Er_5Sr + Ec_5Sc + Em_5Sm + Ew_5CW/Hb + F)\}^{1/2} - Ex_5]/[\{(Eo_2So +$$
$$Er_2Sr + Ec_2Sc + Em_2Sm + Ew_2CW/Hb)(Eo_2So + Er_2Sr + Ec_2Sc +$$
$$Em_2Sm + Ew_2CW/Hb + F)\}^{1/2} - Ex_2]$$

-continued
$$\Phi_{62} = [\{(Eo_6So + Er_6Sr + Ec_6Sc + Em_6Sm + Ew_6CW/Hb)(Eo_6So + \quad (24)$$
$$Er_6Sr + Ec_6Sc + Em_6Sm + Ew_6CW/Hb + F)\}^{1/2} - Ex_6]/[\{(Eo_2So +$$
$$Er_2Sr + Ec_2Sc + Em_2Sm + Ew_2CW/Hb)(Eo_2So + Er_2Sr + Ec_2Sc +$$
$$Em_2Sm + Ew_2CW/Hb + F)\}^{1/2} - Ex_2]$$

In the embodiment, in addition to equations (10) to (12) and (18), the following relationship is established among the tissue terms $Ex_i$ (i=1, 2, 3, 4, 5, and 6):

$$Ex_6 = A_6 Ex_2 + B_6 \quad (25)$$

where $A_6$ and $B_6$ are known.

In this case, the following equation is held:

$$Sr = 1 - So - Sc - Sm \quad (26)$$

By substituting equations (10) to (12), (18), (25), and (26) into equations (20) to (24), simultaneous equations with five unknowns So, Sc, Sm, $Ex_2$, and Hb are obtained. When the simultaneous equations are solved, the values of So, Sc, Sm, $Ex_2$, and Hb can be obtained.

FIG. 6 shows optical absorptive characteristics of various kinds of hemoglobin. For example, light wavelengths used in the embodiments are as follows:

In the first embodiment which measures two kinds of hemoglobin ($O_2$Hb and RHb)

(A) In the case where also the oxygen saturation is obtained and four wavelengths are used Used wavelengths: $\lambda_1$=700 nm, $\lambda_2$=805 nm, $\lambda_3$=890 nm, and $\lambda_4$=1,250 nm (B) In the case where three wavelengths which are little affected by the oxygen saturation are used Used wavelengths: $\lambda_1$=805 nm, $\lambda_2$=890 nm, and $\lambda_3$=1,250 nm In the second embodiment which measures three kinds of hemoglobin ($O_2$Hb, RHb, and COHb) and five wavelengths are used Used wavelengths: $\lambda_1$=660 nm, $\lambda_2$=700 nm, $\lambda_3$=805 nm, $\lambda_4$=890 nm, and $\lambda_5$=1,250 nm In the third embodiment which measures three kinds of hemoglobin ($O_2$Hb, RHb, and MetHb) and five wavelengths are used Used wavelengths: $\lambda_1$=700 nm, $\lambda_2$=750 nm, $\lambda_3$=805 nm, $\lambda_4$=890 nm, and $\lambda_5$=1,250 nm In the fourth embodiment which measures four kinds of hemoglobin ($O_2$Hb, RHb, COHb, and MetHb) and six wavelengths are used Used wavelengths: $\lambda_1$=660 nm, $\lambda_2$=700 nm, $\lambda_3$=850 nm, $\lambda_4$=805 nm, $\lambda_5$=890 nm, and $\lambda_6$=1,250 nm Next, specific apparatuses which are respectively based on the principles of the three embodiments will be described.

Figure 1:
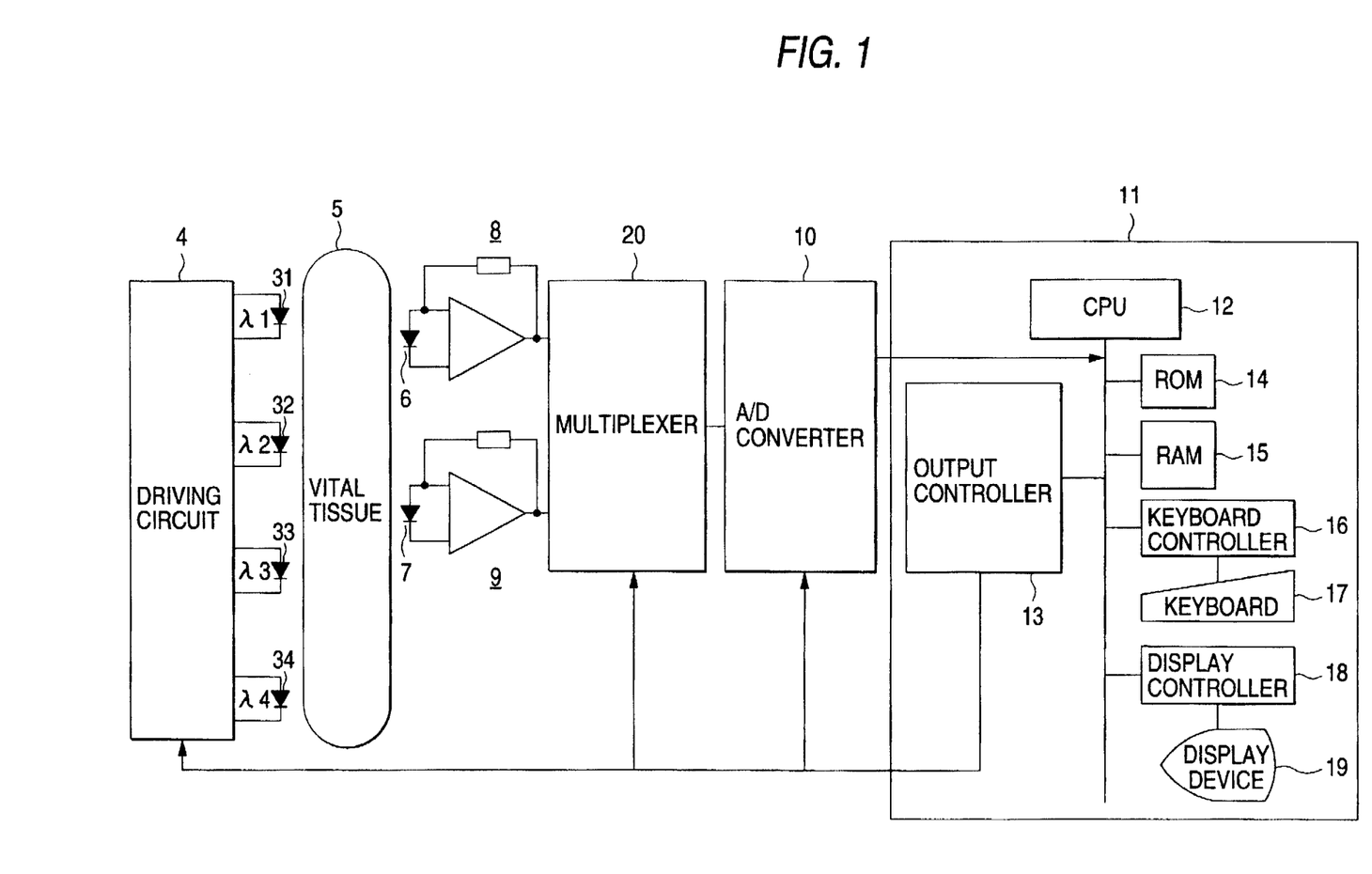
FIG. 1 is a diagram showing the whole configuration of a first embodiment (A).

First, a specific apparatus of the first embodiment (A) will be described. FIG. 1 shows the whole configuration of the apparatus. In the embodiment, the apparatus comprises four light sources 31 to 34. The light sources 31 to 34 are LEDs which emit light of wavelengths of $\lambda_1$=700 nm, $\lambda_2$=805 nm, $\lambda_3$=890 nm, and $\lambda_4$=1,250 nm, respectively. At the wavelength $\lambda_1$=700 nm, oxyhemoglobin and reduced hemoglobin have optical absorption coefficients which are largely different from each other. The intensity of transmitted light of the wavelength depends on the oxygen saturation. At the wavelength $\lambda_4$=1,250 nm, optical absorption of water is very large in degree. A driving circuit 4 drives the four light sources 31 to 34. Light sensors 6 and 7 are placed so as to oppose the light sources 31 to 34, and convert light which is transmitted through vital tissues 5 interposed between the light sources and the sensors, into an electric signal. The light sensor 6 is a silicon photodiode which converts light emitted from the light sources 31 to 33, into an electric signal, and the light sensor 7 is a germanium photodiode which converts light emitted from the light source 34, into an electric signal. Current/voltage transducers 8 and 9 are amplifiers which convert currents flowing through the light sensors 6 and 7 into voltages corresponding to the levels of the currents, respectively. Each of the transducers consists of an operational amplifier and a resistor. A multiplexer 20 selects one of signals output from the current/voltage transducers 8 and 9 and outputs the selected signal. An A/D converter 10 converts the level of the output voltage of the current/voltage transducer 8 or 9 into a digital value. A computer 11 conducts processing based on data supplied from the A/D converter 10 and outputs a control signal for controlling the operation timing to the driving circuit 4 and the multiplexer 20.

The computer 11 comprises: a CPU (Central Processing Unit) 12; an output controller 13, a ROM 14, a RAM 15, a keyboard controller 16, and a display controller 18 which are connected to the CPU 12; a keyboard 17 connected to the keyboard controller 16; and a display device 19 connected to the display controller 18. The output controller 13 controls signals which are output from the computer 11 to external devices. The ROM 14 is a read only memory which stores a program such as that shown in the flowchart of FIG. 2. The RAM 15 is a read/write memory which is used in the execution of the program by the CPU 12. The keyboard 17 has a plurality of keys and, when one of the keys is pressed, outputs a signal corresponding to the pressed key. The keyboard controller 16 conducts a control so that a signal output from the keyboard 17 is supplied to the CPU 12 and stored in the RAM 15. The display device 19 is a device which is, for example, a CRT and displays data supplied to the device on a screen. The display controller 18 produces data for display from data stored in the RAM 15 and supplies the produced data to the display device 19. The CPU 12 executes the program stored in the ROM 14, conducts signal transmission and reception between the CPU and the components so as to control them, and processes data.

In the embodiment, the light sources 31 to 34 and the driving circuit 4 constitute the light irradiating means. The light sensors 6 and 7, the current/voltage transducers 8 and 9, the multiplexer 20, and the A/D converter 10 constitute the photoelectric converting means. In the functions of the computer 11, steps 101 to 105, 109, and 110 shown in FIG. 2 correspond to the density variation calculating means, step 106 corresponds to the density ratio calculating means, and step 107 corresponds to the hemoglobin concentration calculating means.

Figure 2:
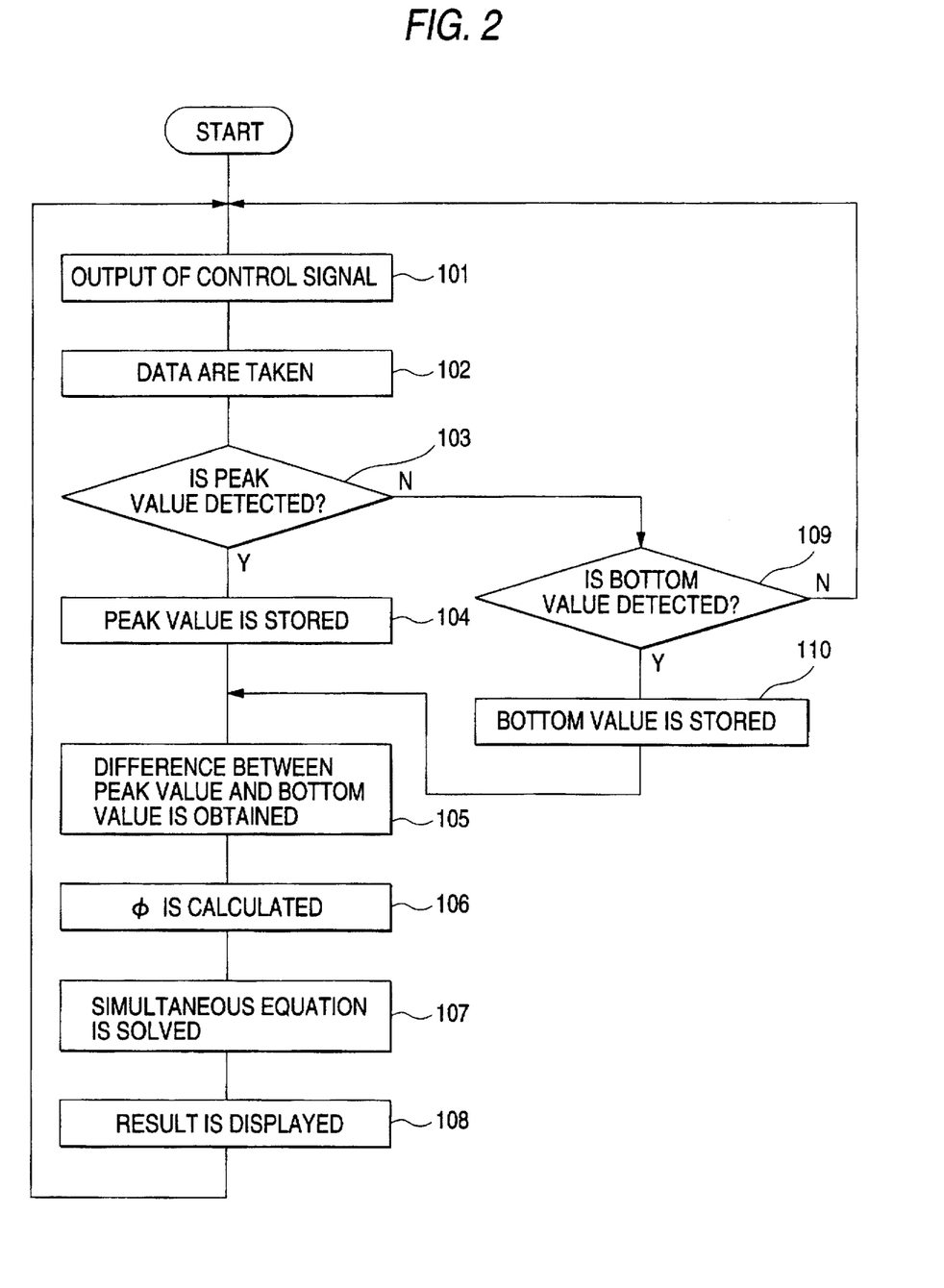
FIG. 2 is a flowchart illustrating the operation of the first embodiment (A).

The operation of the thus configured apparatus will be described with reference to the flowchart of FIG. 2. First, the subject inserts a finger between the light sources 31 to 34 and the light sensors 6 and 7. The fingertip is used as the vital tissues 5 shown in FIG. 1. Then the operator operates the keyboard 17 so as to input a signal for starting the operation of the computer 11. When the operation is started, the CPU 12 outputs in step 101 the control signal to the driving circuit 4 and the A/D converter 10. In response to the signal, the driving circuit 4 causes the light sources 31 to 34 to sequentially emit light. The light emitted from the light sources 31 to 34 is transmitted through the vital tissues 5 and then reaches the light sensor 6 or 7 which in turn converts the light into a current. The resulting current is converted by the current/voltage transducer 8 or 9 into a voltage corresponding to the level of the current. On the other hand, since the multiplexer 20 receives the control signal which is the same as that supplied from the CPU 12 to the driving circuit 4, the multiplexer selects one of the voltages output from the current/voltage transducers 8 and 9 in synchronization with the light emitting timing of the light sources 31 to 34, and outputs the selected voltage to the A/D converter 10. The light sensor 6 is a device in which the sensitivity to light of the wavelengths $\lambda_1=700$ nm, $\lambda_2=805$ nm, and $\lambda_3=890$ nm is very higher than that to light of the wavelength $\lambda_4=1,250$ nm. The light sensor 7 is a device in which the sensitivity to light of the wavelength $\lambda_4=1,250$ nm is very higher than that to light of the wavelengths $\lambda_1=700$ nm, $\lambda_2=805$ nm, and $\lambda_3=890$ nm. During a period when the light sources 31 to 33 emit light, the multiplexer 20 outputs only the output voltage of the current/voltage transducer 8 to the A/D converter 10, and, during a period when the light source 34 emits light, the multiplexer 20 outputs only the output voltage of the current/voltage transducer 9 to the A/D converter 10.

Thereafter, the operation of the CPU 12 proceeds to step 102 in which the output of the A/D converter 10 is acquired and the acquired output is written into the RAM 15.

The operation of the CPU 12 then proceeds to step 103. The data of transmitted light which have been acquired until now are checked to judge whether the level of each wavelength has passed its latest peak or not. If the level of each wavelength has passed the peak, the operation proceeds to step 104 in which the values of the peaks are obtained and then stored in the RAM 15. The operation then proceeds to step 105 so that the difference $\Delta I$ between the detected latest peak and the detected latest bottom is obtained for each wavelength. Thereafter, the operation of the CPU 12 proceeds to step 106 so as to obtain $\Phi_{12}$, $\Phi_{32}$, and $\Phi_{42}$. The operation of the CPU 12 proceeds to step 107 and simultaneous equations (1) to (3) into which $\Phi_{12}$, $\Phi_{32}$, and $\Phi_{42}$ obtained in step 106 and equations (10) to (13) are substituted are calculated so as to obtain the hemoglobin concentration Hb. Thereafter, the operation of the CPU 12 proceeds to step 108 in which the obtained hemoglobin concentration Hb is displayed on the display device 19, and then returns to step 101.

If it is judged in step 103 that the level has not yet passed the peak, the operation of the CPU 12 proceeds to step 109. The data of transmitted light which have been acquired until now are checked to judge whether the level of each wavelength has passed its latest bottom or not. If it is judged that the level has passed the bottom, the operation of the CPU 12 proceeds to step 110 in which the value of the bottom is obtained and stored into the RAM 15, and then proceeds to step 105. If it is judged in step 109 that the level has not yet passed the bottom, the operation of the CPU 12 returns to step 101.

According to the embodiment, the oxygen saturation So can be obtained together with the hemoglobin concentration Hb.

Figure 3:
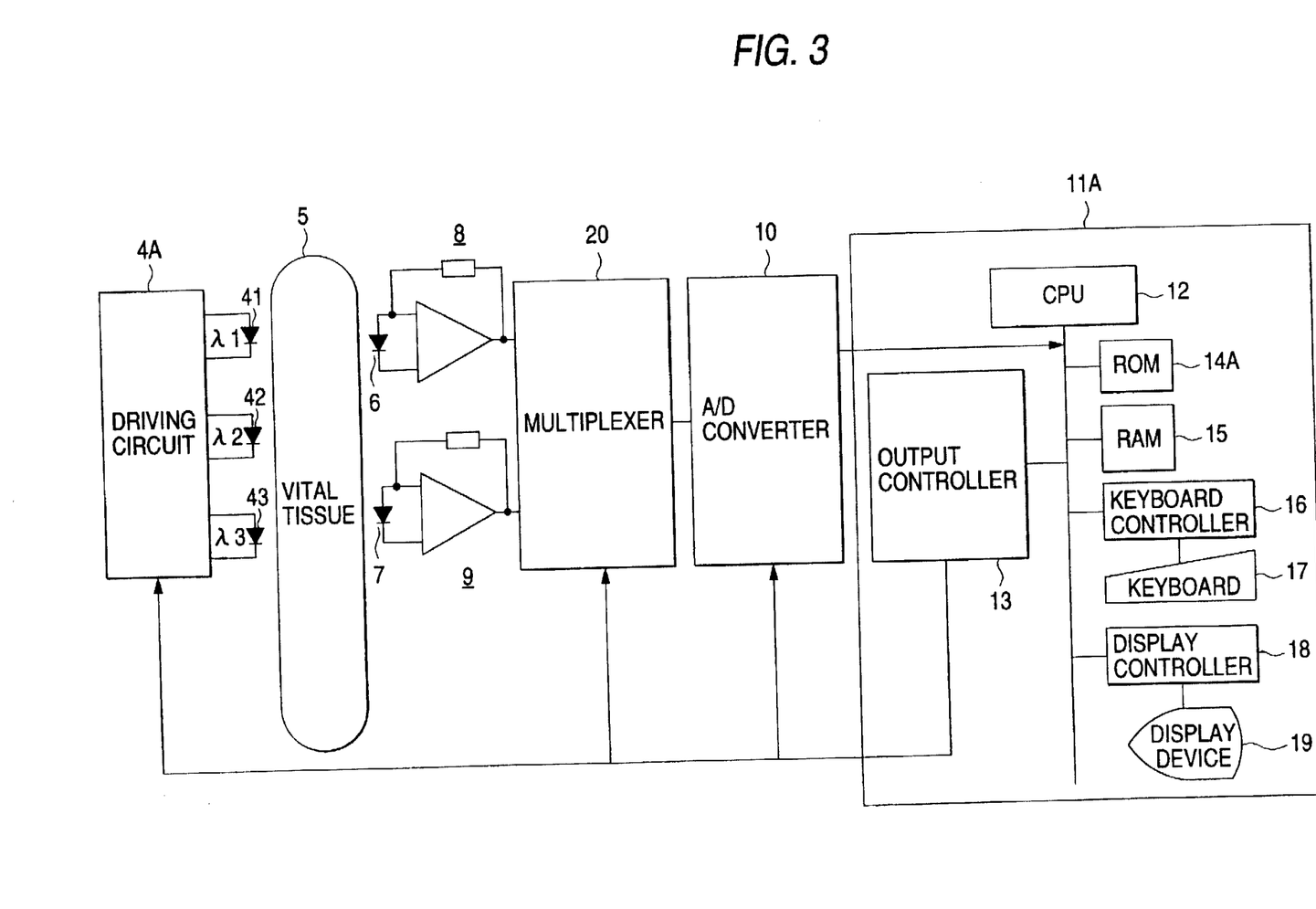
FIG. 3 is a diagram showing the whole configuration of a first embodiment (B).

Next, a specific apparatus of the first embodiment (B) will be described. FIG. 3 shows the whole configuration of the apparatus. In the embodiment, the apparatus comprises three light sources 41 to 43.

The light sources 41 to 43 are LEDs which emit light of wavelengths of $\lambda_1=805$ nm, $\lambda_2=890$ nm, and $\lambda_3=1,250$ nm, respectively. At the wavelengths $\lambda_1$, $\lambda_2$, and $\lambda_3$, optical absorption of oxyhemoglobin is substantially equal to that of reduced hemoglobin. At $\lambda_3=1,250$ nm among the wavelengths, optical absorption of water is very large in degree. A driving circuit 4A drives the light sources 41 to 43. Light sensors 6 and 7 are placed so as to oppose the light sources 41 to 43, and convert light which is transmitted through the vital tissues 5 interposed between the light sources and the sensors, into an electric signal. The light sensor 6 is a silicon photodiode which converts light emitted from the light sources 41 and 42, into an electric signal, and the light sensor 7 is a germanium photodiode which converts light emitted from the light source 43, into an electric signal. A multiplexer 20 and an A/D converter 10 convert the level of the output voltage of current/voltage transducer 8 or 9 into a digital value. A computer 11A conducts processing based on data supplied from the A/D converter 10 and outputs a control signal for controlling the operation timing to the driving circuit 4A and the multiplexer 20.

A ROM 14A of the computer 11A stores a program which is slightly different from that stored in the ROM 14 of the computer 11 of the first embodiment (A) shown in FIG. 1. The program stored in the ROE 14A of the computer 11A is different from that shown in the flowchart of FIG. 2 in that the processes for the four wavelengths in steps 101 to 105, 109, and 110 are replaced with those for the three wavelengths, that the process in step 106 is conducted for obtaining $\Phi_{12}$ and $\Phi_{32}$, and that the process in step 107 is conducted for calculating simultaneous equations (1A) and (2A) into which $\Phi_{12}$ and $\Phi_{32}$ obtained in the previous step and equations (10) and (11) are substituted, thereby obtaining the hemoglobin concentration Hb. The other components of the computer 11A are the same as those of the computer 11.

In the embodiment, the light sources 41 to 43 and the driving circuit 4A constitute the light irradiating means. The light sensors 6 and 7, the current/voltage transducers 8 and 9, the multiplexer 20, and the A/D converter 10 constitute the photoelectric converting means. In the functions of the computer 11A, steps corresponding to steps 101 to 105,109, and 110 shown in FIG. 2 correspond to the density variation calculating means, a step corresponding to step 106 corresponds to the density ratio calculating means, and a step corresponding to step 107 corresponds to the hemoglobin concentration calculating means.

The operation of the thus configured apparatus is approximately similar to that of the first embodiment (A), and hence its description is omitted.

According to the embodiment, since wavelengths which are not affected by the oxygen saturation are used, the total hemoglobin concentration can be obtained by using a reduced number of wavelengths.

Figure 4:
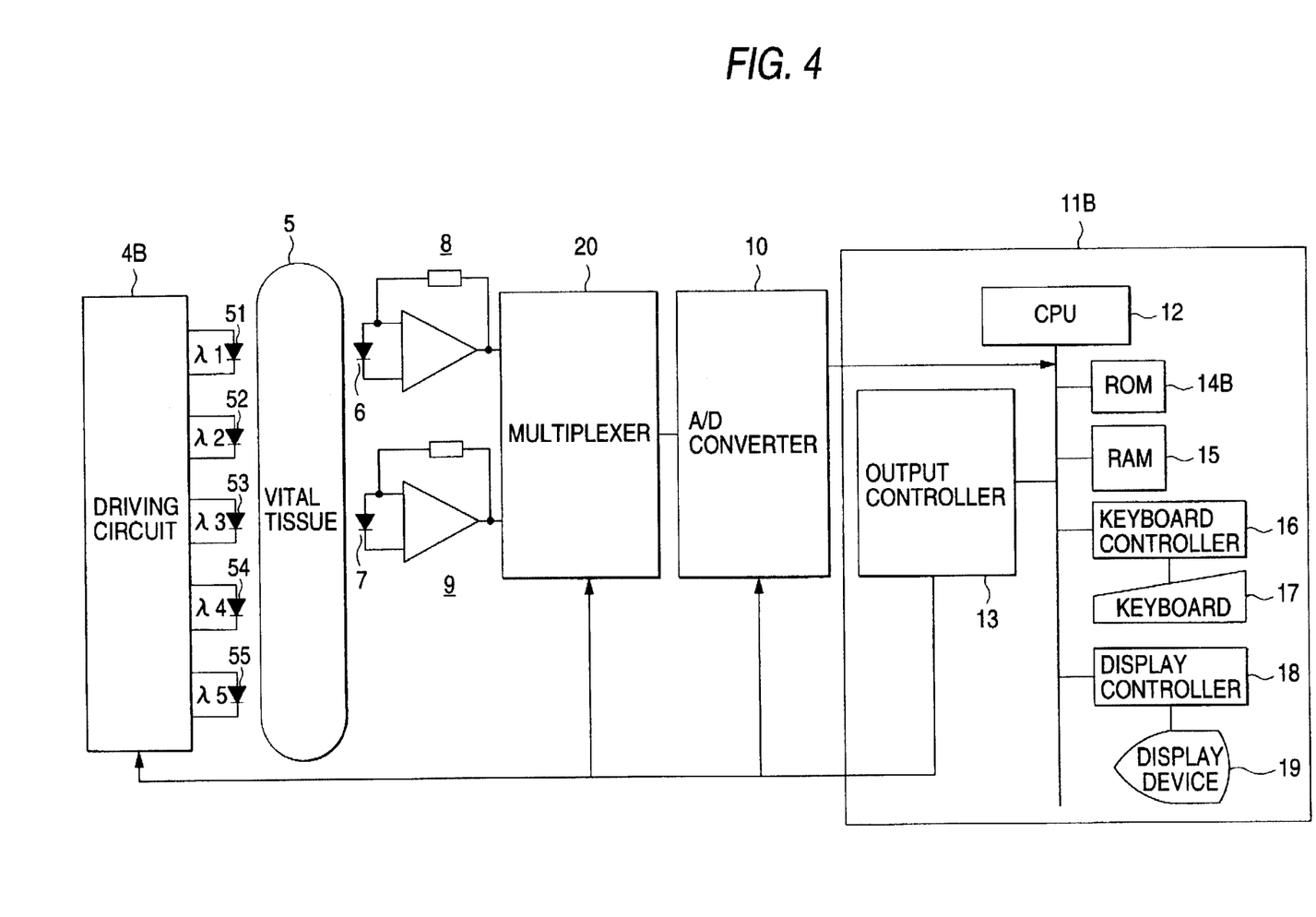
FIG. 4 is a diagram showing the whole configuration of a second embodiment.

Next, a specific apparatus of the second embodiment will be described. FIG. 4 shows the whole configuration of the apparatus. The components which are identical with those of the apparatus of the first embodiment (A) shown in FIG. 1 are designated by the same reference numerals and their description is omitted. In the embodiment, the apparatus comprises five light sources 51 to 55. The light sources 51 to 55 emit light of wavelengths of $\lambda_1$=660 nm, $\lambda_2$=700 nm, $\lambda_3$=805 nm, $\lambda_4$=890 nm, and $\lambda_5$=1,250 nm, respectively. These wavelengths are selected so that the measurement of carboxyhemoglobin is easily conducted. A driving circuit 4B drives the five light sources 51 to 55. Light sensors 6 and 7 are placed so as to oppose the light sources 51 to 55, and converts light which is transmitted through the vital tissues 5 interposed between the light sources and the sensor, into an electric signal. A computer 11B conducts processing based on data supplied from the A/D converter 10 and outputs a control signal for controlling the operation timing to the driving circuit 4B and the multiplexer 20. A ROM 14B of the computer 11B stores a program which is slightly different from that stored in the ROM 14 of the computer 11 of the first embodiment (A) shown in FIG. 1. The other components of the computer 11B are the same as those of the computer 11A.

In the embodiment, the light sources 51 to 55 and the driving circuit 4B constitute the light irradiating means. The light sensors 6 and 7, current/voltage transducers 8 and 9, the multiplexer 20, and the A/D converter 10 constitute the photoelectric converting means.

The operation of the thus configured apparatus is approximately similar to that based on the flowchart of FIG. 2 which has been described in conjunction with the first embodiment (A), but different from that in the following point. In the first embodiment (A), data of transmitted light of four wavelengths are processed. By contrast, in the embodiment, data of transmitted light of five wavelengths are processed. In the step corresponding to step 106 of FIG. 2, four kinds of $\Phi$, i.e., $\Phi_{12}$, $\Phi_{32}$, $\Phi_{42}$, and $\Phi_{52}$ are obtained, and, in the step corresponding to step 107 of FIG. 2, simultaneous equations (14) to (17) into which the obtained $\Phi_{12}$, $\Phi_{32}$, $\Phi_{42}$, and $\Phi_{52}$ and equations (10) to (12), (18), and (19) are substituted are calculated. Therefore, the solutions of the simultaneous equations are So, Sc, Ex$_2$, and Hb. In the step corresponding to step 108 of FIG. 2, the CPU 12 conducts a control so that the calculation results are displayed on the display device 19.

According to the embodiment, in addition to the total hemoglobin concentration Hb, the oxyhemoglobin concentration So, the carboxyhemoglobin concentration Sc, and the reduced hemoglobin concentration Sr (from $Sr=1-So-Sc$) in total hemoglobin can be obtained.

Next, a specific apparatus of the third embodiment will be described. Also in the embodiment, the apparatus comprises five light sources such as shown in FIG. 4. However, the light sources emit light of wavelengths of $\lambda_1$=700 nm, $\lambda_2$=750 nm, $\lambda_3$=805 nm, $\lambda_4$=890 nm, and $\lambda_5$=1,250 nm, respectively. These wavelengths are selected so that the measurement of methemoglobin is easily conducted. The other components are the same as those of the apparatus of the first embodiment (A), and hence their description and illustration are omitted.

The operation of the thus configured apparatus is approximately similar to that of the first embodiment (A), but different from that in the following point. In the first embodiment (A), simultaneous equations (14) to (17) are calculated in the step corresponding to step 107 of FIG. 2. By contrast, in the embodiment, simultaneous equations (14A) to (17A) are calculated. When equations (10) to (12), (18), and (19A) are used, simultaneous equations with four unknowns So, Sm, Ex$_2$, and Hb are obtained. Consequently, the solutions of the simultaneous equations are So, Sm, Ex$_2$, and Hb.

According to the embodiment, in addition to the total hemoglobin concentration Hb, the oxyhemoglobin concentration So, the methemoglobin concentration Sm, and the reduced hemoglobin concentration Sr (from $Sr=1-So-Sm$) in total hemoglobin can be obtained.

Figure 5:
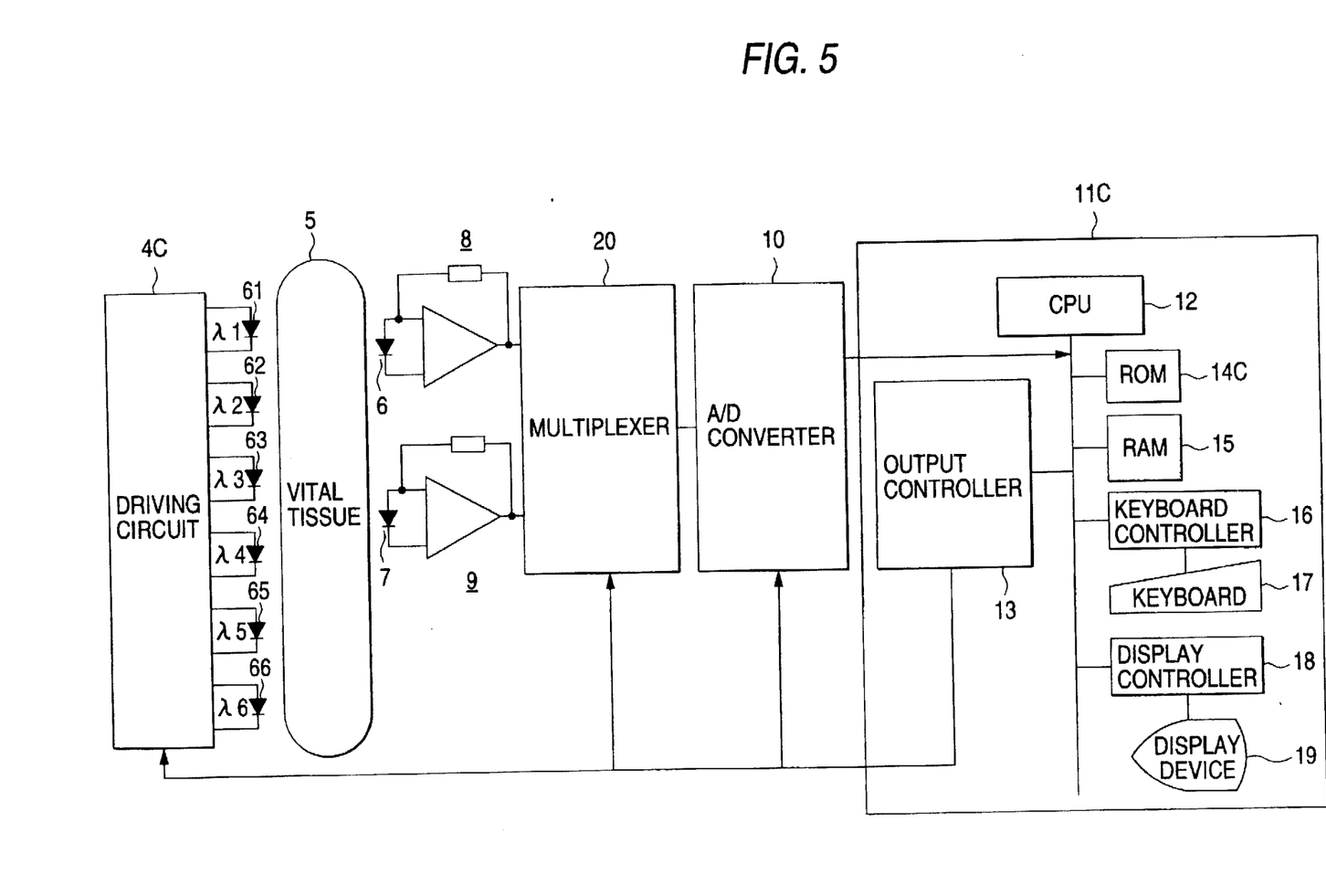
FIG. 5 is a diagram showing the whole configuration of the fourth embodiment.

Next, a specific apparatus of the fourth embodiment will be described. FIG. 5 shows the whole configuration of the apparatus. The components which are identical with those of the apparatus of the first embodiment (A) are designated by the same reference numerals and their description is omitted. In the embodiment, the apparatus comprises six light sources 61 to 66. The light sources 61 to 66 emit light of wavelengths of $\lambda_1$=660 nm, $\lambda_2$=700 nm, $\lambda_3$=850 nm, $\lambda_4$=805 nm, $\lambda_5$=890 nm, and $\lambda_6$=1,250 nm, respectively. The wavelengths have features described above. A driving circuit 4C drives the six light sources 61 to 66. Light sensors 6 and 7 are placed so as to oppose the light sources 61 to 66, and converts light which is transmitted through the vital tissues 5 interposed between the light sources and the sensor, into an electric signal. A computer 11C conducts processing based on data supplied from the A/D converter 10 and outputs a control signal for controlling the operation timing to the driving circuit 4C and the multiplexer 20. A ROM 14C of the computer 11C stores a program which is slightly different from that stored in the ROM 14 of the computer 11 of the first embodiment (A) shown in FIG. 1. The other components of the computer 11C are the same as those of the computer 11A.

In the embodiment, the light sources 61 to 66 and the driving circuit 4C constitute the light irradiating means. The light sensors 6 and 7, current/voltage transducers 8 and 9, the multiplexer 20, and the A/D converter 10 constitute the photoelectric converting means.

The operation of the thus configured apparatus is approximately similar to that based on the flowchart of FIG. 2 which has been described in conjunction with the first embodiment (A), but different from that in the following point. In the first embodiment (A), data of transmitted light of four wavelengths are processed. By contrast, in the embodiment, data of transmitted light of six wavelengths are processed. In the step corresponding to step 106 of FIG. 2, five kinds of $\Phi$, i.e., $\Phi_{12}$, $\Phi_{32}$, $\Phi_{42}$, $\Phi_{52}$, and $\Phi_{62}$ are obtained, and, in the step corresponding to step 107 of FIG. 2, simultaneous equations (20) to (24) into which the obtained $\Phi_{12}$, $\Phi_{32}$, $\Phi_{42}$, $\Phi_{52}$, and $\Phi_{62}$ and equations (10) to (12), (18), (25), and (26) are substituted are calculated. Therefore, the solutions of the simultaneous equations are So, Sc, Sm, $Ex_2$, and Hb. In the step corresponding to step 108 of FIG. 2, the CPU 12 conducts a control so that the calculation results are displayed on the display device 19.

According to the embodiment, in addition to the total hemoglobin concentration Hb, the oxyhemoglobin concentration So, the carboxyhemoglobin concentration Sc, the methemoglobin concentration Sm, and the reduced hemoglobin concentration Sr (from $Sr=1-So-Sc-Sm$) in total hemoglobin can be obtained.

As described above, according to the invention, since the optical density of light of a wavelength which can be optically absorbed by water is used and equations in which the variation in thickness of the tissue layers is considered are used, the absolute value of the hemoglobin concentration can be measured noninvasively and continuously.

What is claimed is:

1. An apparatus for measuring hemoglobin, comprising:

light irradiating means for irradiating vital tissue with light having different wavelengths, at least one of the wavelengths being optically absorbed by water;

photoelectric converting means for converting light which is emitted from said light irradiating means and transmitted through the vital tissues into an electric signal;

optical density variation calculating means for obtaining an optical density variation for each of the wavelengths from pulsation of an output of said photoelectric converting means, the optical density variation corresponding to the difference between pulsation of light transmitted through the tissue due to blood and pulsation of light transmitted through the tissue due to the tissue;

optical density ratio calculating means for obtaining a ratio of optical density variations for the wavelengths which are obtained by said optical density variation calculating means; and hemoglobin concentration calculating means for obtaining a total hemoglobin concentration from an output of said optical density ratio calculating means.

* * * * *